US008409798B2

(12) United States Patent
Luy et al.

(10) Patent No.: US 8,409,798 B2
(45) Date of Patent: Apr. 2, 2013

(54) SCREENING METHOD FOR IDENTIFYING PUFA PKS IN SAMPLES

(75) Inventors: Markus Luy, Ried-Brig (CH); Matthias Rüsing, Köln (DE)

(73) Assignee: Nutrinova Nutrition Specialties & Food Ingredients GmbH, Frankfurt (DE)

( * ) Notice: Subject to any disclaimer, the term of this patent is extended or adjusted under 35 U.S.C. 154(b) by 299 days.

(21) Appl. No.: 11/547,948

(22) PCT Filed: Apr. 8, 2005

(86) PCT No.: PCT/EP2005/003702
§ 371 (c)(1),
(2), (4) Date: Oct. 6, 2006

(87) PCT Pub. No.: WO2005/098033
PCT Pub. Date: Oct. 20, 2005

(65) Prior Publication Data
US 2007/0259355 A1    Nov. 8, 2007

(30) Foreign Application Priority Data

Apr. 8, 2004  (DE) .................. 10 2004 017 369

(51) Int. Cl.
*C12Q 1/68* (2006.01)
(52) U.S. Cl. ........................................ 435/6.1
(58) Field of Classification Search .................. None
See application file for complete search history.

(56) References Cited

U.S. PATENT DOCUMENTS

| 6,566,583 | B1 * | 5/2003 | Facciotti et al. | ............... | 800/281 |
| 7,211,418 | B2 * | 5/2007 | Metz et al. | ................. | 435/134 |

FOREIGN PATENT DOCUMENTS

| EP | 0823475 A1 | 2/1998 |
| WO | WO 9803671 A1 | 1/1998 |
| WO | WO 00/42195 A2 | 1/2000 |
| WO | WO 02/083870 A2 | 10/2002 |

OTHER PUBLICATIONS

Gentile et al. Journal of Applied Microbiology vol. 95:1124-1133. 2003.*
Lowe et al. Nucleic Acids Research vol. 18:1757-1761. 1990.*
Artemis P. Simopoulos, "Essential Fatty Acids in Health and Chronic Disease," Am.J.Clin.Nutr., American Society for Clinical Nutrition (USA), p. 560S-569S, (1999).
Ronald A. Hites, et al., "Global Assessment of Organic Contaminants in Farmed Salmon,"Science, vol. 303, p. 226-229, (Jan. 9, 2004).
Howard Sprecher, "Metabolism of Highly Unsaturated n-3 and n-6 Fatty Acids," Biochimica et Biophysica Acta 1486, Elsevier Science B.V., p. 219-231, (2000).
James G. Wallis et al., "Polyunsaturated Fatty Acid Synthesis: What Will They Think of Next?" Trends in Biochemical Sciences, vol. 27 (No. 9), p. 467-473, (Sep. 2002).
Leonard Katz et al., "Polyketide Synthesis: Prospects for Hybrid Antibiotics," Annu.Rev.Microbiol., 47 ed., p. 875-912, (1993).
Haruko Takeyama et al., "Expression of the Eicosapentaenoic Acid Synthesis Gene Cluster from *Shewanella sp.* in a Transgenic Marine Cyanobacterium, *Synechococcus sp.*," Microbiology, 143 ed., p. 2725-2731, (1997).
David A. Hopwood et al., "Molecular Genetics of Polyketides and Its Comparison to Fatty Acid Biosynthesis," Annu.Rev.Genet., 24 ed., p. 37-66, (1990).
James G. Metz et al., "Production of Polyunsaturated Fatty Acids by Polyketide Synthases in Both Prokaryotes and Eukaryotes," Science, p. 290-293, (Jul. 13, 2001).
G. Gentile et al., "*Shewanella sp.* GA-22, A Psychrophilic Hydrocarbonoclastic Antarctic Bacterium Producing Polyunsaturated Fatty Acids," Journal of Applied Microbiology, No. 95, p. 1124-1133, (2003).
David S. Nichols et al., "Biomarker Techniques to Screen for Bacteria That Produce Polyunsaturated Fatty Acids," Journal of Microbiological Methods, 48 ed., p. 161-170, (2002).
Xiao Qiu, "Identification of a Δ4 Fatty Acid Desaturase from *Thraustochytrium sp.* Involved in the Biosynthesis of Docosahexanoic Acid by Heterologous Expression in *Saccharomyces cerevisiae* and *Brassica juncea*," The Journal of Biological Chemistry, vol. 276, No. 34, p. 31561-31566, (Aug. 24, 2001).

* cited by examiner

*Primary Examiner* — Christopher M. Babic
(74) *Attorney, Agent, or Firm* — Hammer & Associates, P.C.

(57) ABSTRACT

The invention relates to a method for the rapid and simple identification of PUFA PKS in microorganisms. Said method is characterized by the fact that DNA sections representing PKS that produce specifically for PUFA (polyunsaturated fatty acids) are reproduced in vitro. The PUFA PKS-specific amino acid sequence LGIDSIKRVEIL makes it possible to derive oligonucleotides which are used for the efficient PCR screening for PUFA PKS genes or PUFA-producing microorganisms. The inventive method is particularly suitable for the high throughput screening of microorganisms for PUFA PKS genes.

6 Claims, 2 Drawing Sheets

Figure 2:

```
FASTX compares a DNA sequence to a protein sequence data bank version 3.4t21
May 14, 2003

Pearson et al, Genomics (1997) 46:24-36

1>>>Sequence - 357 aa
vs  SWISS-PROT All library
414613972 residues in 1289149 sequences FASTX (3.46 May 2003) function [optimized, BL50 matrix (o=15:-5:-1)] ktup: 2
  join: 37, opt: 31, open/ext: -12/-2 shift: -20, width: 16

The best scores are:                                          opt bits E(1289149)

SWALL:Q94FB8 Q94FB8 Polyunsaturated fatty acid  (2910) [f]    604 113.5 9.4e-23
SWALL:O33904 O33904 Hypothetical protein (Acyl   (2756) [f]    309  63.8 7.8e-08
SWALL:Q9RA21 Q9RA21 Genes, similar to eicosape   (2652) [f]    292  60.9 5.5e-07
SWALL:Q93CG8 Q93CG8 Omega-3 polyunsaturated fa   (2573) [f]    208  46.8 0.0097
SWALL:Q93HH9 Q93HH9 Modular polyketide synthas   (2365) [f]    200  45.4 0.023
SWALL:Q8YWG7 Q8YWG7 Heterocyst glycolipid synt   (1263) [f]    196  44.5 0.024

>>SWALL:Q94FB8 Q94FB8 Polyunsaturated fatty acid synthas  (2910 aa)
 initn: 357 init1: 357 opt: 604  Z-score: 550.6  bits: 113.5 E(): 9.4e-23
Smith-Waterman score: 608;  89.516% identity (94.068% ungapped) in 124 aa overlap
(1-357:1815-1937)

10        40        70       100       130       160
Sequen LGIDSIKRVEILSEVQAMLNVEAKDVDALSRTRTVGEVVNATKAEIASSS----GAAAPA
       :::::::::::::::::::::::::::::::::::::::::: ::::::..    .::::
SWALL: LGIDSIKRVEILSEVQAMLNVEAKDVDALSRTRTVGEVVDAMKAEIAGSSAPAPAAAAPA
            1820      1830      1840      1850      1860      1870

190       220       250       280       310       340
Sequen PAAAVAPAP-AAAPAVSSALLEKAESVVMEVLAAKTGYETDMIEADMELETELGIDSIKR
       :::: ::::  :::::::::::::::.::::::::::::::::::.::::::::::::::
SWALL: PAAA-APAPAAAAPAVSSELLEKAETVVMEVLAAKTGYETDMIESDMELETELGIDSIKR
            1880      1890      1900      1910      1920      1930

Sequen VEIL
       ::::
SWALL: VEIL
```

SCREENING METHOD FOR IDENTIFYING PUFA PKS IN SAMPLES

The invention describes a method for the rapid and simple identification of PUFA-PKS genes (PUFA=polyunsaturated fatty acids; PKS=polyketide synthase) in samples such as, e.g., biomass, especially in microorganisms. It is characterized by an in vitro reproduction of DNA sections specific for PUFA-producing PKS. The invention is also based, in addition to the identification of the appropriate DNA sequences, on the establishment of the experimental conditions for their multiplication.

The term PUFAs (polyunsaturated fatty acids) denotes multiply unsaturated long-chain fatty acids with a chain length>C12 and at least two double bonds. There are two main families of PUFA, which differ according to the position of the first double bond, relative to the alkyl end, in omega-3 and in omega-6 fatty acids. They are important components of cell membranes, where they are present in the form of lipids, especially phospholipids. PUFAs also function as preliminary stages of important molecules in humans and in animals such as, g, prostaglandins, leukotrienes and prostacyclins (A. P. Simopoulos, essential fatty Acids in health and chronic disease, Am. J. Clin. Nutr. 1999 (70), pp. 560-569). Important representatives of the group of omega-3 fatty acids are DHA (docosahexaenoic acid) and EPA (eicosapentaenoic acid), which can be found in fish oils and in marine microorganisms. An important representative of omega-6 fatty acids is ARA (arachidonic acid) that occurs, e.g., in filamentous fungi but can also be isolated from animal tissues such as liver and kidney. DHA and ARA occur next to one another in human mother's milk.

PUFAs are essential for a human as regards an appropriate development, in particular for the developing brain, tissue formation and its repair. Thus, DHA is an important component of human cell membranes, especially those of the nerves. Furthermore, DNA plays an important part in the maturing of brain function and is essential for the development of vision. Omega-3 PUFAs such as DHA and EPA are used as nutrient supplement since a balanced nourishment with a sufficient supply of DHA is advantageous for the prophylaxis of certain diseases (A. P. Simopoulos, Essential fatty acids in health and chronic disease, American Journal of Clinical Nutrition 1999 (70), pp. 560-569). For example, adults with non-insulin-dependent diabetes exhibit a deficiency or at least an unbalanced DHA balance related to cardiac problems occurring later. Likewise, neuronal diseases such as, e.g., Alzheimer's or schizophrenia are accompanied by low DHA levels. There is a large number of sources for the commercial extraction of DHA, such as, e.g., oils from marine cold-water fish, egg yolk fractions or marine microorganisms. Microorganisms suitable for the extraction of n-3 PUFA are found, e.g., in bacteria in the in the genus *Vibrio* (e.g., *Vibrio marinus*) or in the dinoflagellates (*Dinophyta*), in which in particular the genus *Crypthecodinium*, such as *C. cohnii* or in the Stramenopiles (or *Labyrinthulomycota*), such as the *Pinguiophyceae* such as, e.g., *Glossomastix, Phaeomonas, Pinguiochrysis, Pinguiococcus* and *Polypodochrysis*. Other preferred microorganisms for producing PUFA belong in particular to the order *Thraustochytriales*, (*Thraustchytriidea*) with the genera *Japonochytrium, Schizochytrium, Thraustochytrium, Althornia, Labyrinthuloides, Aplanochytrium* and *Ulkenia*. Microorganisms of the genera *Mortierella, Entomophthora, Phytium* and *Porphyridium* are used for the commercial production of ARA.

Commercially used sources for PUFA such as plants or animals are often characterized by a very heterogeneous composition of the oils extracted from them. The oils extracted in this manner must be subjected to expensive purification processes in order to be able to enrich one or several PUFAs. The supplying with PUFA from such sources is also subjected to uncontrollable fluctuations. Thus, disease and weather influences can reduce animal and also vegetable yields. The extraction of PUFA from fish is subject to seasonal fluctuations and can even be temporarily sharply limited due to overfishing or climatic changes (e.g., el Niño). Animal oils, especially fish oils, can accumulate noxious substances from the environment via the food chain. It has become known that animals are highly stressed by organochlorides such as, e.g., polychlorinated biphenyls, in particular in commercial fish farms, that counteract the healthy aspects of fish consumption (Hites et al. 2004, Global assessment of organic contaminants in farmed salmon, Science 303, pp. 226-229). The resulting loss in quality of fish products results in a decreasing acceptance of consumers for fish and fish oils as omega-3 PUFA sources. Furthermore, the purification of DHA from fish is relatively expensive on account of high technical requirements. On the other hand, DHA is present in a few marine microorganisms in amounts of approximately 50% of the total fat component of the cell and they can be cultivated relatively economically in large fermenters. Another advantage of microorganisms is a composition of the oils extracted from them that is limited to a few components.

Two different biocatalytic paths are known for the biosynthesis of long-chain PUFA. In the case of the so-called Sprecher Pathway, long-chain PUFAs such as DHA and EPA are synthesized starting from palmitic acid by a stream of elongation- and desaturation steps and terminating shortenings (H. Sprecher, Metabolism of highly unsaturated n-3 and n-6 fatty acids. Biochimica et Biophysica Acta 1486 (2000) pp. 219-231). This biosynthesis path is taken as described or in a similar manner in most organisms, even in humans and in plants. However, a certain number of marine organisms takes a different biosynthesis path for the production of EPA and DHA. These PUFA-producing microorganisms include marine representatives of gamma proteobacteria and, up to the present, the eukaryotic protist *Schizochytrium*. They synthesize long-chain PUFA via so-called polyketide synthases (PKS). These PKSs represent large enzymes that catalyze the synthesis of secondary metabolites consisting of ketide units (G. W. Wallis, J. L. Watts and J. Browse, Polyunsaturated fatty acid synthesis: what will they think of next? Trends in Biochemical Sciences 27 (9) (2000) pp. 467-473). The synthesis of polyketides contains a number of enzymatic reactions that are analogous to those of fatty acid synthesis (Hopwood & Sherman Annu. Rev. Genet. 24 (1990) pp. 37-66; Katz & Donadio Annu. Rev. of Microbiol. 47 (1993) pp. 875-912).

Gene sequences of different PUFA-PKSs (PUFA-synthesizing PKSs) are already known. Thus, a 38 kb genomic fragment was isolated from the marine bacterium *Shewanella* sp. that contains the information for the production of eicosapentaenoic acid (EPA). It was possible to produce EPA in *E. coli* and in *Synechoccus* by the transfer of the gene clusters contained in the genomic fragment. Subsequent sequencing of this fragment resulted in the identification of 8 open reading frames (ORFs. Open reading frames) (H. Takeyama et al., Microbiology 143 (1997) pp. 2725-2731). Five of these open reading frames from *Shewanella* are closely related to polyketide synthase genes. Further PKS-like gene clusters were also found in other PUFA-producing marine bacteria such as, e.g., *Vibrio marinus* (M. Tanaka, et al. 21 (1999) pp. 939-945). Analogous PUFA-producing, PKS-like ORFs were also able to be identified in the eukaryotic protist *Schizochytrium* (Metz et al, Science 293 (2001) pp. 290-293 and WO 00/42195). Three ORFs were determined in *Schizochytrium* that display partial identities with the EPA gene cluster from *Shewanella*. The existence of these preserved PKS genes in a few prokaryotes and the eukaryote *Schizochytrium* furnishes an indication for a possible horizontal gene transfer of PUFA-PKS genes between pro- and eukaryotes.

Very little is still known at present about the distribution of PKS between the individual species. Thus, e.g., a phylogenetically close relative of *Schizochytrium*, the marine protist *Thraustochytrium* sp., appears to have no PKS even though it is rich in DHA like *Schizochytrium*. It produces long-chain PUFA, among other things, using a very seldom occurring delta-4 desaturase (X Qiu et al. J. Biol. Chem. (2001) pp. 31561-31566). Both, *Thraustochytrium* and *Schizochytrium*, belong to the order *Thraustochytriales* but have totally different biosynthesis paths for the production of long-chain PUFA. Therefore, there is great interest in determining the distribution of PUFA-PKS genes in marine microorganisms, especially as regards the discovery of new potential PUFA producers for the possible production of individual PUFAs on a commercial scale. In addition, there is currently a need for especially efficient screening methods in order to examine the large number of marine microorganisms with a high throughput for PUFA producers. Furthermore, a knowledge of many different PUFA-PKS should furnish information about the gene arrangement and structure of the corresponding enzymes and therewith for the production of different PUFAs. This is particularly important for many further applications such as, e.g., for the production of PUFA in transgenic microorganisms or plants. Designer oils with different PUFA combinations could be produced transgenically by the variation of genes.

Patent application WO 02/083870 A2 describes a method for identifying organisms containing the PUFA-PKS genes. It is based on the one hand on five selection criteria concerning the fatty acid spectrum that should be given under certain cultivation conditions in order to function as indicator for a PUFA-PKS system. The more selection criteria are met, the stronger the indication for a PUFA-PKS system. It is based on the other hand on Southern blot analyses in which restriction-cleaved genomic DNA transferred onto blot membranes is hybridized from potential PUFA-PKS candidates (meeting of the five selection criteria) with PUFA-PKS-specific nucleic acid sequences. This second detection step was subsequently expanded in the exemplary embodiment for the verification of the result to the screening of a genomic DNA bank. Moreover, patent application WO 02/083870 describes strategies for the enrichment and selection of suitable microorganisms as a pre-selection for the above-cited screening method.

However, it is apparent for those skilled in the art that the screening method described in WO 02/083870 A2 is very expensive and therefore unsuitable for a high-throughput screening. Moreover, the evaluation of the selection parameters in the first screening step appears to be very vague, which can potentially result in negative results in the second screening step.

The present invention therefore had the task in view of the state of the art of making available a method for identifying PUFA-PKS genes in different microorganisms. The method should make possible a broad screening of microorganisms efficiently, economically and in a short time. The screening should take place with a high throughput without expensive sample preparation.

This task as well as other ones not explicitly cited but which can be readily derived or concluded from the initially discussed contexts in this document are solved by the subject matter defined in the claims of the present invention.

An advantageous method for identifying PUFA-PKS genes in microorganisms is made available by the method defined in Claim 1. This method comprises the in vitro amplification of nucleic acids from samples, preferably biomass, especially from microorganisms, by means of polymerase chain reaction (PCR: polymerase chain reaction) using degenerated oligonucleotides (primers) derived from the amino acid succession LGIDSIKRVEIL (SEQ ID No. 5). A nucleic acid sequence derived from the amino acid succession LGIDSIKRVEIL (SEQ ID No. 5) represents, e.g., the sequence succession 5'-CTC GGC ATT GAC TCC ATC MG CGT GTC GAG ATT CTC-3' (SEQ ID No. 6). The use in accordance with the invention of the degenerated primers described here leads to the identification of PKS gene fragments in PUFA-producing microorganisms.

The method in accordance with the invention surprisingly makes do with oligonucleotides derived from only this one amino acid sequence section cited above.

Furthermore and amazingly, heavily degenerated oligonucleotides containing a large number of N bases or, e.g., inosines, can be largely dispensed with.

The method contains all oligonucleotides that can be derived from the above-cited amino acid sequence LGIDSIKRVEIL (SEQ ID No. 5) for amplifying and identifying PUFA-PKS genes. The selection of the oligonucleotides is independent of the length of the selected partial sequence and of its orientation (sense or antisense or complementary or non-complementary).

In a preferred form oligonucleotides with a length of 10-36 bp, preferably 15-25 bp and especially preferably 18 bp are used in the detection method of the invention.

The amount of oligonucleotides used can vary as long as there is no negative effect on the detection method for PUFA-PKS present. This also applied to all other components used in the PCR reaction.

In a preferred embodiment the hybridization of the oligonucleotides used takes place at an annealing temperature of 45° C.-65° C., preferably 50° C.-60° C. and especially preferably at 53° C.-57° C.

The duration of the individual phases of the PCR, that is, of the denaturing, of the annealing and of the elongation can also vary as long as there is no negative effect on the detection method for PUFA-PKS present.

The number of PCR cycles can also vary but is preferably between 20 and 40 cycles, especially preferably between 25 and 35 cycles and quite especially preferably approximately 30 cycles.

All isolatable DNA and RNA nucleic acids from the microorganisms to be investigated as well as cDNA generated from mRNA can be used as template for the PCR. In a special embodiment entire cells or biomass can also be used as template for the PCR.

In a further embodiment the oligonucleotides in accordance with the invention can also be used as hybridization probes for detecting complementary nucleic acid sequences.

In particular, the method in accordance with the invention is suitable for a high throughput screening of microorganisms for PUFA-PKS genes.

Accordingly, the present invention also comprises a nucleic acid obtainable (identifiable) with the method of:
(1) A method for the demonstration of PUFA-PKS gene-specific nucleic acid sequences in samples, in which (a) A polymerase chain reaction (PCR) is performed using specific oligonucleotides and with a small part of the sample as a template, and (b) Obtained PCR products are sequenced and the obtained sequence information is compared with databanks in order to identify new PUFA-PKS sequence information by partial agreement with already known sequences, characterized in that the oligonucleotides used are derived from the amino acid sequence LGID-SIKRVEIL.

(2) The method according to (1) above, characterized in that the oligonucleotides are degenerated.

(3) The method according to (1) above, characterized in that the length of the oligonucleotides is 10-36 bp.

(4) The method according to (1) above, characterized in that the amount of oligonucleotides used is preferably approximately 20 pmol.

(5) The method according to (1) above, characterized in that the annealing temperature is approximately 45-65° C.

(6) The method according to (1) above, characterized in that the number of cycles is approximately 20-40.

(7) The method according to (1) above, characterized in that nucleic acids isolated from the biomass or the biomass itself being used as template for the PCR.

or by using the nucleic acid sequences derivable from SEZ ID No. 5 as hybridization probes.

A microorganism containing a nucleic acid obtainable (identifiable) with the methods of (1) through (7) above or by using the nucleic acid sequences derivable from SEZ ID No. 5 is also comprised.

Regardless of the great demand for PUFA-producing microorganisms, prior to the present invention there was no known efficient detection method based on PCR for identifying PUFA-PKS-containing microorganisms. A paper by Gentile et al. does describe the possible use of oligonucleotides for the amplification of PUFA-PKS gene sequences; however, the oligonucleotides described it are not derived from the ACP domains or from the amino acid sequence LGID-SIKRVEIL on which the invention is based (Gentile et al. 2003 J. Appl. Microbiol. (95) pp. 1124-1133).

It is suspected that the amplification of a sequence section (APC domains of PKS) already present in multiple copy is the basis of the high efficiency of the PCR method described here. The presence of a large number of target sequences at the beginning of the PCR probably results in an increase of the efficiency. This results for its part in a higher hit ratio during screening. However, it was very surprising that specifically PUFA-PKS genes were able to be isolated with the aid of oligonucleotides derived from the amino acid sequence LGIDSIKRVEIL since APC domains occur in quite a number of other genes, e.g., PKS not specific for PUFA as well as peptide synthases and fatty acid synthases in general. This is also viewed as the reason that cloning tests of PUFA-PKS genes with derivation of oligos from the LGIDSIKRVEIL sequence were previously not attempted.

Otherwise, up to the present only much more time-consuming and less reliable screening methods based on biomarkers for identifying PUFA producers were developed (D. S. Nichols and T. A. McMeekin 2002 J. Microbiol. Methods 48 (2-3), pp. 161-170).

FIG. 2 shows the sequence homology of the PCR product (ACP domain), amplified with oligonucleotides, derived from the sequence LGIDSIKRVEIL, and from *Ulkenia* sp. SAM 2179 to the PUFA-PKS from *Schizochytrium*.

Figure 1:
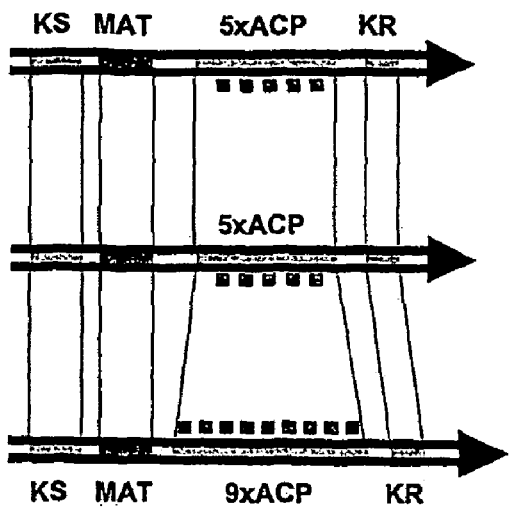
FIG. 1 shows a comparison of the position and number of the acyl carrier protein domains of a few previously known PUFA-PKSs from *Moritella marina, Photobacterium profundum* (strain SS9) and *Schizochytrium*. The number of repetitions of the preserved sequence LGIDSIKRVEIL is also shown.

The detection method constituting the basis of the method in accordance with the invention is described in the following using a few examples. However, the detection method and the invention are not limited to these examples.

EXAMPLES

Example 1

Amplification of a PUFA-PKS-specific Sequence from Isolated DNA from *Ulkenia* sp. SAM2179

1.1 Isolation of Genomic DNA 50 ml DH1 medium (50 g/l glucose; 12.5 g/l yeast extract; 16.65 g/l Tropic Marin; pH 6.0) was inoculated in a 250 ml Erlenmeyer flask with flow spoiler with *Ulkenia* sp. SAM 2179 (*Ulkenia* spec BP-5601; WO9803671) and cultivated 48 h at 28° C. and 150 rpm. The cells were subsequently washed with sterile tap water, centrifuged off and the cell sediment frozen at −85° C. A cell mass of approximately 1.25 g dry weight was achieved. For the further workup the cell sediment was then transferred into a mortar and comminuted under liquid nitrogen with a pestle to a fine powder. Then, approximately $^1/_{10}{}^{th}$ of the pulverized cell material was compounded with 2 ml lysis buffer (50 mM tris/Cl pH 7.2; 50 mM EDTA; 3% (v/v) SDA; 0.01% (v/v) 2-mercaptoethanol) and incubated 1 h at 68° C. 2 ml phenol/chloroform/isoamylalcohol (25:24:1) were subsequently added, agitated and centrifuged 20 min at 10000 rpm. After removal of the upper aqueous phase the latter was transferred into two new reaction vessels at 600 µl each and again compounded with 600 µl each phenol/chloroform/isoamylalcohol (25:24:1), agitated and centrifuged 15 min at 13000 rpm. Each 400 µl of a particular upper phase was then transferred into a new reaction vessel and inverted two to three times after the addition of 1 ml ethanol (100%) in each instance. Then, the precipitated DNA was wound on a glass rod, washed with 70% ethanol, dried and dissolved in 50 µl $H_2O_{dist.}$, compounded with 2 µl RNase A and stored at 4° C.

1.2 PCR Reaction Using Motive-Specific Oligonucleotides

The PCR primers MOF1 and MOR1 were used as motive-specific oligonucleotides.

MOF1: 5'-CTC GGC ATT GAC TCC ATC-3' (Seq ID No. 7)

MOR1: 5'-GAG AAT CTC GAC ACG CTT-3' (Seq ID No. 8)

The genomic DNA from *Ulkenia* sp. SAM2179 described as in 1.1 was diluted 1:100. 2 µl of this dilution were then transferred into a 50 µl volume PCR reaction mixture (1× buffer (Sigma); dNTPs (200 µM each); MOF1 (20 pmol), MOR1 (20 pmol) and 2.5 U Taq-DNA polymerase (Sigma). The PCR was carried out under the following conditions: Initial denaturing 94° C. for 3 min, followed subsequently by 30 cycles at 94° C. each for 1 min, 55° C. for 1 min, 72° C. 1 min and finally 8 min 72° C. The PCR products were then analyzed by gel electrophoresis and fragments with an appropriate size incorporated into vector pCR2.1 TOPO via T/A cloning (Invitrogen). After transformation of *E. coli* TOP 10F', plasmid DNA was isolated (Qiaprep Spin, QUAGEN) and sequenced.

The sequence data obtained (SEQ ID No. 1) was compared with the officially accessible EMBL Nucleotide Sequence Database and evaluated. The sequence comparisons obtained with FASTAX yielded for the main product of the PCR from *Ulkenia* sp. SAM 2179 a partial identity, that was approximately 90% on the amino acid level, with the acyl carrier protein of PUFA-PKS (ORF A; ORF: open reading frame) from *Schizochytrium* sp. ATCC 20888 (FIG. 7). Surprisingly, only a single PCR experiment had to be carried out in order to determine this PUFA-PKS in *Ulkenia* sp. SAM 2179.

Example 2

Amplification of a PUFA-PKS-Specific Sequence from Isolated DNA from *Schizochytrium* sp. SR21

2.1 Isolation of Genomic DNA 50 ml DH1 medium (50 g/l glucose; 12.5 g/l yeast extract; 16.65 g/l Tropic Marin; pH 6/0) was inoculated in a 250 ml Erlenmeyer flask with flow spoiler with *Schizochytrium* sp. SR21 (*Schizochytrium* spec., MYA-1381; EP0823475) and cultivated 48 h at 28° C. and 150 rpm. The cells were subsequently washed twice with tap water, centrifuged off and the cell sediment frozen at −85° C. A cell mass of approximately 1.4 g dry weight was obtained. Then, for the further workup the cell sediment was transferred into a mortar and treated as previously described (example 1) for isolating the genomic DNA.

2.2 PCR Reaction Using Motive-Specific Oligonucleotides

The PCR primers MOF1 and MOR1 (see example 1) were used as motive-specific oligonucleotides.

The PCR took place as described in 1.2 with 2 µl genomic DNA from *Schizochytrium* sp. SR21.

The sequence data obtained (SEQ ID No. 2) was compared with the officially accessible EMBL Nucleotide Sequence Database and evaluated. The sequence comparisons obtained with FASTAX yielded for the main product of the PCR from *Schizochytrium* sp. SR21 an approximately 90% partial identity with the acyl carrier protein of the PUFA-PKS (ORF A; ORF: open reading frame) from *Schizochytrium* sp. ATCC 20888. Surprisingly, only a single PCR experiment had to be carried out also for determining this PUFA-PKS in *Schizochytrium* sp. SR21.

Example 3

Amplification of a PUFA-PKS-Specific Sequence Directly from the Biomass of *Schizochytrium* sp. SR21

3.1 Obtention of Biomass 50 ml DH1 medium (50 g/l glucose; 12.5 g/l yeast extract; 16.65 g/l Tropic Marin; pH 6/0) was inoculated in a 250 ml Erlenmeyer flask with flow spoiler with *Schizochytrium* sp. SR21 and cultivated 48 h at 28° C. and 150 rpm. The cells were subsequently washed twice with tap water and centrifuged off. The biomass obtained in this manner was subsequently added directly into a corresponding PCR reaction.

3.2 PCR Reaction Using Motive-Specific Oligonucleotides

The PCR primers MOF1 and MOR1 (see example 1) were used as motive-specific oligonucleotides.

An aliquot of the biomass from *Schizochytrium* sp. SR21 obtained in 3.1 was taken up with a sterile toothpick and transferred into a 50 µl by volume PCR reaction mixture (1× buffer (Sigma); dNTPs (200 µM each); MOF1 (20 pmol), MOR1 (20 pmol) and 2.5U Taq DNA polymerase (Sigma). The PCR was performed as described in point 1.2.

The sequence data obtained (SEQ ID No. 2) was compared with the officially accessible EMBL Nucleotide Sequence Database and evaluated. The sequence comparisons obtained with FASTAX yielded for the main product of the PCR from *Schizochytrium* sp. SR21 an approximately 90% partial identity with the acyl carrier protein of the PUFA-PKS (ORF A; ORF: open reading frame) from *Schizochytrium* sp ATCC 20888. The sequence of the PCR product obtained from the biomass of *Schizochytrium* was identical to that in example 2.

Surprisingly, only a single PCR experiment had to be carried out even here for determining the PUFA-PKS from the biomass of *Schizochytrium* sp. SR21.

Example 4

Amplification of a PUFA-PKS-Specific Sequence Directly from the Biomass of Different *Ulkenias*

4.1 Obtention of Biomass 50 ml DH1 medium (50 g/l glucose; 12.5 g/l yeast extract; 16.65 g/l Tropic Marin; pH 6/0) was inoculated in a 250 ml Erlenmeyer flask with flow spoiler with either *Ulkenia* sp. SAM 2179 or *Ulkenia visurgensis* or another *Ulkenia* sp. and cultivated 48 h at 28° C. and 150 rpm. The cells were subsequently washed twice with tap water and centrifuged off. The biomass obtained in this manner was subsequently added directly into an appropriate PCR reaction.

4.2 PCR Reaction Using Motive-Specific Oligonucleotides

The PCR primers MOF1 and MOR1 (see example 1) were used as motive-specific oligonucleotides.

Aliquots of the biomasses from different ulkenias obtained in 4.1 were taken up with a sterile toothpick and each transferred into a 50 µl by volume PCR reaction mixture (1× buffer (Sigma); dNTPs (200 µM each); MOF1 (20 pmol), MOR1 (20 pmol) and 2.5U Taq DNA polymerase (Sigma). The PCR was performed as described in point 1.2.

The sequence data obtained (SEQ ID No. 1, 3 and 4) was compared with the officially accessible EMBL Nucleotide Sequence Database and evaluated. The sequence comparisons obtained with FASTAX yielded high partial identities with the acyl carrier protein of the PUFA-PKS (ORF A; ORF: open reading frame) from *Schizochytrium* sp. ATCC 20888. The sequence of the PCR product obtained from the biomass of *Ulkenia* sp. SAM 2179 was identical to that in example 1.

Surprisingly, only a single PCR experiment had to be carried out even here each time for determining the particular PUFA-PKS from the biomass of different ulkenias.

The invention claimed is:

1. A method for the demonstration of PUFA-PKS (polyunsaturated fatty acids-polyketide synthase) gene-specific nucleic acid sequences in samples, consisting essentially of the steps:
   (a) performing a polymerase chain reaction (PCR) using degenerated oligonucleotide primers for amplifying the ACP domain and nucleic acids obtained from said sample as a template, and
   (b) sequencing obtained PCR products and comparing the obtained sequence information with databanks in order to identify new PUFA-PKS sequence information by partial agreement with already known sequences, characterized in that the used degenerated oligonucleotide primers for amplifying the ACP domain are obtained from oligonucleotides encoding amino acid sequence LGIDSIKRVEIL (SEQ ID NO: 5).

2. The method according to claim 1, characterized in that the oligonucleotides are degenerated.

3. The method according to claim 1, characterized in that the length of the oligonucleotides is 10-36 bp.

4. The method according to claim 1, characterized in that the amount of oligonucleotides used is about 20 pmol.

5. The method according to claim 1, characterized in that the annealing temperature of the PCR is about 45-65° C.

6. The method according to claim 1, characterized in that the number of cycles of the PCR is about 20-40.

* * * * *

SEQUENCE LISTING

<160> NUMBER OF SEQ ID NOS: 8

<210> SEQ ID NO 1
<211> LENGTH: 357
<212> TYPE: DNA
<213> ORGANISM: Ulkenia sp.

<400> SEQUENCE: 1

```
ctcggcattg actccatcaa gcgtgtcgag attctctctg aggtccaggc tatgcttaac    60
gttgaggcca agatgttga tgctcttagc cgcacccgca ccgttggtga ggttgtcaac   120
gccacgaagg ctgagattgc tagcagctct ggtgctgctg ccctgctcc ggctgctgcc   180 gttgcaccgg cccctgctgc tgccctgct gtcagcagcg ctctccttga aaggccgaa    240 tctgttgtca tggaggttct cgccgccaag actggttacg agactgacat gattgaggcc   300
gacatggagc tcgagactga gctcggcatt gactccatca gcgtgtcga gattctc     357
```

<210> SEQ ID NO 2
<211> LENGTH: 321
<212> TYPE: DNA
<213> ORGANISM: Schizochytrium sp.
<220> FEATURE:
<221> NAME/KEY: misc_feature
<222> LOCATION: (149)..(149)
<223> OTHER INFORMATION: n is a, c, g, or t
<400> SEQUENCE: 2

```
ctcggcattg actccatcaa gcgtgtcgag attctctctg aggtccaggc tatgcttaac    60
gttgaggcca aggatgttga tgctcttagc cgcacccgca ccgttggtga ggttgtcaac   120
gccatgaagg ctgagattgc tagcagctnt ggtgctgctg ccctgctcc tgctgctgcc   180 gctgcaccgg cccctgctgc tgccctgct gtcagcagcg ctctccttga aaggccgaa    240 tctgttgtca tggaggttct cgccgccaag actggttacg agactgacat gattgaggcc   300
gacatggagc tcgagactga g                                             321
```

<210> SEQ ID NO 3
<211> LENGTH: 372
<212> TYPE: DNA
<213> ORGANISM: Ulkenia visurgensis
<400> SEQUENCE: 3

```
ctcggcattg actccatcaa acgtgtcgag atcctcagtg aggtgcaggc caagctgaac    60
gtagaggcca aagacgtcga tgcactcagc cgcactcgta ccgtaggtga ggtcgtcgac   120
gcaatgaagg ccgagataca aggatcgccg agtgggtctc ctgctcctcc aaatgctccg   180
aaactgtcta gcccagtctc atccacacca gctccaacca agttaatctc aaccagcacg   240
ctagcaatgg ccgagtctgt ggttatggag gtccttgccg caaagactgg ctacgaaccg   300
gacatgatcg aggcggacat ggagctcgag accgagctcg gcattgactc catcaagcgt   360
gtcgagattc tc                                                       372
```

<210> SEQ ID NO 4
<211> LENGTH: 372
<212> TYPE: DNA
<213> ORGANISM: Ulkenia sp.

<400> SEQUENCE: 4

```
ctcggcattg actccatcaa acgtgtcgag atcctcagtg aggtgcaggc caagctgaac    60
gtagaggcca aagacgtcga tgcactcagc cgcactcgga ccgtaggtga ggtcgtcgac   120
gcaatgaagg ccgagataca aggatcgccg agtggctctc ctgctcctcc aagtgctccg   180
aaactgtcta gcccagtctc atcctcacca gccccaacca agttaatctc aaccagcacg   240
ctagcaatgg ccgagtctgt ggttatggag gtccttgccg caaagactgg ctacgaaccg   300
gacatgatcg aggcggacat ggagctcgag actgagcttg gcattgactc catcaagcgt   360
gtcgagattc tc                                                       372
```

```
<210> SEQ ID NO 5
<211> LENGTH: 12
<212> TYPE: PRT
<213> ORGANISM: Ulkenia sp.

<400> SEQUENCE: 5

Leu Gly Ile Asp Ser Ile Lys Arg Val Glu Ile Leu
1               5                   10

<210> SEQ ID NO 6
<211> LENGTH: 36
<212> TYPE: DNA
<213> ORGANISM: artificial sequence
<220> FEATURE:
<223> OTHER INFORMATION: Synthetic Construct

<400> SEQUENCE: 6
ctcggcattg actccatcaa gcgtgtcgag attctc                              36

<210> SEQ ID NO 7
<211> LENGTH: 18
<212> TYPE: DNA
<213> ORGANISM: artificial sequence
<220> FEATURE:
<223> OTHER INFORMATION: Synthetic Construct

<400> SEQUENCE: 7
ctcggcattg actccatc                                                  18

<210> SEQ ID NO 8
<211> LENGTH: 18
<212> TYPE: DNA
<213> ORGANISM: artificial sequencez
<220> FEATURE:
<223> OTHER INFORMATION: Synthetic Construct

<400> SEQUENCE: 8
gagaatctcg acacgctt                                                  18
```